United States Patent

Angelucci et al.

[11] Patent Number: 5,571,785
[45] Date of Patent: Nov. 5, 1996

[54] BIOLOGICALLY ACTIVE COMPOUNDS

[75] Inventors: Francesco Angelucci, Milan; Maria Grandi, Reggio Emilia; Antonino Suarato, Milan, all of Italy

[73] Assignee: Farmitalia Carlo Erba S.r.l, Milan, Italy

[21] Appl. No.: 351,474

[22] PCT Filed: Apr. 8, 1994

[86] PCT No.: PCT/EP94/01100

§ 371 Date: Dec. 20, 1994

§ 102(e) Date: Dec. 20, 1994

[87] PCT Pub. No.: WO94/26311

PCT Pub. Date: Nov. 24, 1994

[30] Foreign Application Priority Data

May 11, 1993 [GB] United Kingdom ............... 9309663.4

[51] Int. Cl.[6] ............ A61K 38/16; A61K 31/70; C07K 9/00; C07H 15/24
[52] U.S. Cl. ................. 514/8; 514/34; 530/322; 536/6.4
[58] Field of Search ............... 536/6.4; 514/34, 514/8; 530/322

[56] References Cited

U.S. PATENT DOCUMENTS

| | | | |
|---|---|---|---|
| 4,642,335 | 2/1987 | Miyashiro et al. | 530/409 |
| 5,162,512 | 10/1992 | King et al. | 536/64 |
| 5,169,937 | 12/1992 | Clark et al. | 530/327 |
| 5,387,578 | 2/1995 | Angelucci et al. | 514/21 |

*Primary Examiner*—Elli Peselev
*Attorney, Agent, or Firm*—Oblon, Spivak, McClelland, Maier & Neustadt, P.C.

[57] ABSTRACT

The present invention provides polymer-bound anthracyclines of formula A which consists essentially of three units represented by formulae 1, 2 and 3:

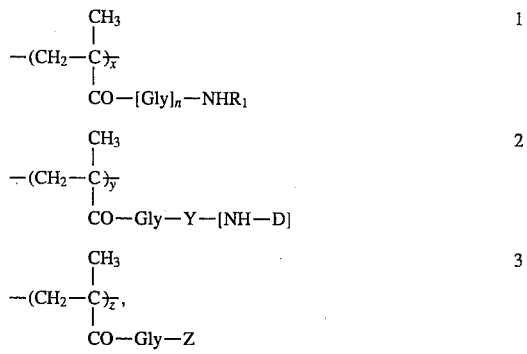

wherein:
Gly represents glycine;
n is 0 or 1;
x is from 70 to 98 mol %,
y is from 1 to 29 mol %,
z is from 1 to 29 mol %,
$R_1$ is a $C_1$–$C_6$ alkyl group substituted by one or more hydroxy groups;
Y is an amino acid residue or a peptide spacer;
[NH—D] is the residue of an anthracycline aminoglycoside [$NH_2$—D]; and
Z is a hydroxy group or a residue of formula —$NHR_1$ wherein $R_1$ is as defined above. Methods for their preparation and pharmaceutical compositions containing them are also provided.

15 Claims, No Drawings

BIOLOGICALLY ACTIVE COMPOUNDS

This is a national phase application of International application No. PCT/EP94/01100, filed Apr. 8, 1994.

The present invention relates to soluble synthetic polymer-bound anthracyclines, to their preparation and to pharmaceutical compositions containing them.

Doxorubicin, 4'-epidoxorubicin and 4-demethoxydaunorubicin are examples of anthracyclines which are known from the prior art and which are currently used in the clinical treatment of neoplastic malignancies; see for example, F. Arcamone: "Doxorubicin" Medicinal Chemistry monograph, vol 17, Academic Press 1981.

Many polymeric derivatives of doxorubicin, endowed with antitumour activity, have been prepared. Amongst these, a particularly promising candidate for clinical development is soluble polymer-bound doxorubicin, which consists of hydrophilic moieties and peptide chains to which doxorubicin and 2-hydroxypropylamine are linked. This polymer-bound-doxorubicin derivative is prepared by condensing doxorubicin hydrochloride with a methacrylic polymeric precursor containing peptidyl chains, activated as the p-nitrophenyl ester, in dimethylsulfoxide in the presence of triethylamine followed by aminolysis of the remaining ester groups with 1-amino-2-hydroxypropane. Incubation of this material with rat lysosomal enzymes (tritosomes) cleaves the amidic bond between the terminal amino acid and doxorubicin [J.Kopecek et al., Biomaterials 10, 335 (1989); R.Duncan et al., Biochem. Pharmacol., 39 1125 (1990); R.Duncan et al., J.Controlled Release 10, 51 (1989); 18 123 (1992) and 19 331 (1992)].

A problem with conventional processes, for example as described above, is that it can be difficult to remove the doxorubicin from the doxorubicin polymer conjugate. This is due to the formation of π-complexes between bound and free doxorubicin; the material has been shown to behave as one entity in dialysis, molecular filtration and gel chromatography [J. Feijen et al., J. Controlled Release 1, 301 (1985)].

The polymer-bound-anthracycline systems of the present invention are based on methacrylic polymers bearing hydrophilic moieties, peptidyl pendant chains linked only to the amino group of anthracycline and residues of glycine, either in the form of free acid or in the form of amide derivative. These systems have the advantage over the prior art that the anthracycline may be easily released from the polymer to which it is bound. In addition, the polymer-bound anthracyclines of the invention have broader antitumour activity and lower general toxicity than the corresponding free anthracyclines.

Accordingly, the present invention provides a polymer-bound anthracycline of formula A which consists essentially of three units represented by formulae 1, 2 and 3:

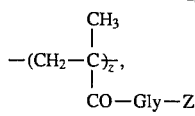

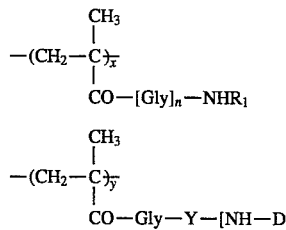

wherein:

Gly represents glycine;

n is 0 or 1;

x is from 70 to 98 mol %, y is from 1 to 29 mol %, z is from 1 to 29 mol %, $R_1$ is a $C_1$–$C_6$ alkyl group substituted by one or more hydroxy groups;

Y is an amino acid residue or a peptide spacer;

[NH—D] is the residue of an aminoglycoside anthracycline [NH$_2$—D]; and

Z is hydroxy or a residue of formula —NHR$_1$ as defined above.

The aminoglycoside anthracycline of which [NH—D] is a residue is represented herein as [NH$_2$—D] wherein D denotes the structure of an anthracycline aminoglycoside minus the amino group of the sugar moiety.

The polymer-bound anthracycline preferably contains the units 1 in a range of from 90 to 98 mol %, the units of formula 2 from 1 to 10 mol % and the units of formula 3 from 1 to 10 mol %.

The enzymatic in vivo hydrolysis of the peptidyl chains gives rise to the release of only the active drug D—NH$_2$, whilst unit 3 remains intact.

Suitable alkyl groups which $R_1$ may represent are $C_1$–$C_4$ alkyl groups substituted by one or more hydroxy groups; examples include hydroxyethyl, 2-hydroxypropyl and 3-hydroxypropyl groups.

The peptide spacer Y should be susceptible to intracellular hydrolysis. The spacer may be resistant to extracelluar hydrolysis. The peptide spacer may be from 1 to 10, for example 2 to 4, amino acid residues long. Typically the peptide spacer is a tripeptide or a tetrapeptide.

Each of the constituent amino acid residues of the peptide spacer Y which is chiral may be present as either the D or the L optical isomer, or as a D/L mixture. The conventional three letter system of denoting amino acids is employed herein, wherein the symbols denote the L configuration of the chiral amino acid unless otherwise stated. The peptide spacer Y may be present as a racemic mixture or as an optically pure isomer.

Preferably Y is selected from Gly-Phe-Gly, Gly-Leu-Gly, Phe-Leu-Gly, Gly-Phe-Leu-Gly, or Leu-Leu-Gly with the glycyl residue in each case being bound to the aminoglycoside anthracycline.

The aminoglycoside anthracycline residue [NH—D] is suitably the residue of an anthracycline aminoglycoside [NH$_2$—D] of the following formula Q:

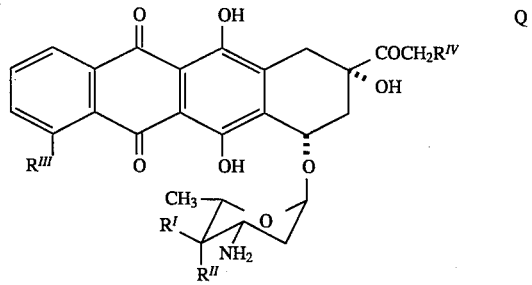

wherein one of $R^I$ and $R^{II}$ is hydrogen and the other is a hydroxy group or iodine; $R^{III}$ is hydrogen or OCH$_3$ and $R^{IV}$ is hydrogen or a hydroxy group.

Preferred examples of the anthracycline aminoglycoside [NH$_2$—D] are: doxorubicin, 4'-epidoxorubicin, 4-demethoxydaunorubicin, idarubicin and 4'-iodo, 4'-desoxy doxorubicin.

The invention also provides a process for the preparation of a polymer-bound anthracycline A which consists essentially of the units 1, 2 and 3 as defined above. The process comprises:

i) reacting a polymeric intermediate B, wherein B consists essentially of units of the following formulae 1 and 4:

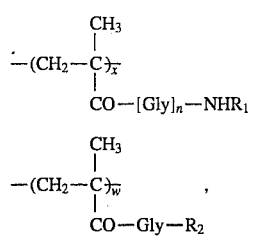

1

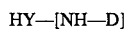

4 wherein x, n and R$_1$ in formula 1 are as defined above, w is from 30 to 2 mol % and R$_2$ is a hydroxy group or a leaving group, with an anthracycline derivative of general formula 5

HY—[NH—D]   5 wherein [NH—D] and Y are as defined above; and ii) when it is desired to prepare a polymer-bound anthracycline wherein Z is the unit of formula 3 is NHR$_1$, reacting the product of step (i) wherein R$_2$ is a leaving group with a compound of formula NH$_2$R$_1$ in which R$_1$ is as defined above.

The leaving group which R$_2$ may represent is suitably a phenyloxy group which is substituted on the phenyl ring by one or more electron-withdrawing groups. Examples of suitable electron-withdrawing groups include nitro (—NO$_2$) and halogen. R$_2$ is preferably the leaving group

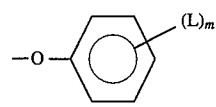

wherein L is an electron withdrawing group, for example —NO$_2$ or a halogen such as fluorine or chlorine, and m is an integer of 1 to 5, typically 1 to 3, preferably 1 or 2. Preferably R$_2$ is a p-nitrophenoxy group or a 2,4-dichlorophenoxy group.

Compounds of formula 5 are easily separated from the polymeric conjugate of formula A owing to their high lipophilicity. Thus, as discussed above the present approach to the preparation of polymer-bound-anthracyclines overcomes a major drawback of the conventional condensation of anthracyclines with polymers, namely the difficulty in separating free anthracycline from the polymer-conjugate.

The polymeric intermediates B consisting essentially of units 1 and 4, as defined above, are prepared by the radical copolymerization of methacryloyl compounds of the following formulae 6 and 7:

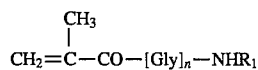

6

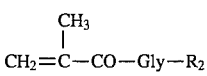

7 wherein n, R$_1$ and R$_2$ are as defined above.

Some polymers consisting essentially of units 1 and 4 are known from the literature; for example a polymer B1 consisting of units 1 in which R$_1$ represents —CH$_2$CH(OH)CH$_3$, n=0 and units 4 in which R$_2$ represents a p-nitrophenol residue is prepared by radical precipitation copolymerization of N-(2-hydroxypropyl)methacrylamide [6a:R$_1$=CH$_2$CH(OH)CH$_3$, n=0] with N-methacryloylglycyl p-nitrophenylester [7a: R$_2$=O—C$_6$H$_4$pNO$_2$], as described in J. Kopecek, Makromol. Chem 178, 2159 (1977)]. Polymeric intermediates consisting of units 1 and 4 in which R$_2$ represents hydroxy may be prepared by radical homogeneous polymerization.

Some monomers of formulae 6 and 7 are known. Compounds of formula 6 in which n=0 and R$_1$ is an alkyl-bearing secondary hydroxy group are generally prepared by reacting methacryloyl chloride with aliphatic amine bearing secondary hydroxy groups. On the other hand, compounds of formula 6 in which n=0 and R$_1$ is the residue of an alkyl-bearing primary hydroxy group, may be prepared from methacrylic acid and amino compounds in the presence of a condensing agent such as 1-ethoxycarbonyl-2-ethoxy-1,2-dihydroquinoline.

The peptidyl-anthracycline derivatives of formula 5 are a further aspect of the present invention. Methods for their preparation are known. For example, since it is important to react a suitable N-protected peptide with anthracycline, the N-protecting peptidyl group must be selected from those that are removed in conditions capable conferring stability on the anthracycline. An example is the triphenylmethyl group.

The peptidyl anthracycline derivatives of formula 5 may be prepared by a process which comprises (i) reacting an N-protected peptide of formula 8 or 9:

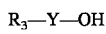   8

   9 wherein R$_3$ is an acid sensitive protecting amino group, P is a leaving group, and Y is an amino acid residue or a peptide spacer as defined above, with an anthracycline aminoglycoside [NH$_2$—D] as defined above to produce an intermediate of general formula 10:

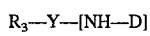   10 wherein [NH—D], Y and R$_3$ are as defined above; and (ii) removing the protecting group R$_3$ to yield the peptidyl-anthracycline 5 in the form of a free base.

P may be a leaving group as defined and exemplified above for R$_2$. In addition P may be a pentafluorophenyloxy or N-hydroxy-succinimido group. Examples of the acid sensitive protecting group R$_3$ include trityl and diphenylamino groups.

Peptidyl derivatives of formula 8 and 9 are prepared following standard synthetic procedures that are known from peptide literature. Protection of the amino function with an acid sensitive group such as triphenylmethyl is typically performed according to Theodoropoulos et al., [J.Org. Chem. 47, 1324 (1982)]. The reaction conditions followed for the preparation of compounds 8, 9 and 10 are designed in order to avoid racemization; the resultant peptidyl derivatives are therefore in the same configuration of the starting amino acids.

In order to prepare anthracycline derivatives of formula 5, compound 9 may be reacted with an anthracycline hydrochloride salt in an anhydrous polar solvent such as dimethylformamide in the presence of equivalent amounts of an organic base such as triethylamine, for example at room temperature for 15 hours, to give an intermediate of formula 10 that is purified by chromatography and then deblocked to derivative of formula 5, for example in aqueous 75% acetic acid at room temperature.

It should be noted that the reaction of anthracyclines bearing a hydroxy group at position C-14, such as doxorubicin and 4'-epidoxorubicin in the form of hydrochloride salt, with activated peptidyl derivatives of formula 9, in the presence of the organic based needed to deblock the 3'-amino group of the anthracyclines, in a polar solvent, affords a mixture of derivative 10 and anthracyclines substituted both at the amino group of the sugar moiety and at the C-14 position. The bis(3'—N,14—O—peptidyl)derivatives are removed from the mixture by chromatography.

Compounds of formula 10 may be also prepared by condensing an N-protected peptide of formula 8 with an anthracycline in the form of the hydrochloride salt, in a dry polar solvent such as dimethylsulfoxide in the presence of an equivalent amount of condensing agent such as 1-ethoxycarbonyl-2-ethoxy-1,2-dihydroquinoline. This procedure does not afford bis-peptidyl derivatives of anthracyclines bearing a C-14 hydroxy groups.

The condensation of intermediate B with peptidyl anthracycline derivatives of formula 5, optionally followed by displacement of the remaining leaving groups, affords polymer-bound anthracyclines consisting essentially of units 1, 2 and 3. It should be stressed that this procedure avoids formation of ester bonds between primary hydroxy groups and pendant glycyl activated esters.

Polymer-bound drugs of formula A in which residue Z of unit 3 represents a group of formula $NHR_1$, as previously defined, are preferably prepared by reacting intermediate B in which $R_2$ is a leaving group as defined above, with an anthracycline derivative of formula 5 in an anhydrous polar organic solvent such as dimethylformamide or dimethylsulfoxide. The reaction can typically be effected for from 8 to 24 hours. The reaction is typically carried out at a temperature from 15° C. to 30° C., preferably at room temperature for 15 hours, then the remaining leaving groups are displaced by reacting the conjugate with a compound of formula $NH_2R_1$, as above defined, for a time of 0.5 to 3 hours at room temperature.

Polymer-bound drugs of formula A in which residue Z of unit 2 represents a hydroxy group, are preferably prepared by reacting intermediate B in which $R_2$ is hydroxy with an anthracycline derivative of formula 5 in an anhydrous polar organic solvent such as dimethylformamide or dimethylsulfoxide. The reaction can typically be effected for from 8 to 24 hours. The reaction is typically carried out at a temperature from 15° to 30° C., preferably at room temperature for 15 hours.

For example, in order to prepare a polymer-bound anthracycline in which Z is a residue $NHR_1$, as defined above, an intermediate B in which $R_2$ is a leaving group such as p-nitrophenoxy is treated with a peptidyl anthracycline 5 at room temperature for 15 hours. B is suitably employed at 14% w/v and 5 at 2.3% w/v. A compound of formula $NH_2R_1$, as defined above, is then added, typically at 0.1% w/v, and the reaction mixture is kept at room temperature for 3 hours. The conjugate is precipitated with acetone, dissolved with absolute ethanol, typically at a concentration of 8% (w/w), and precipitated again with acetone to give the desired polymer-bound anthracycline.

In the process described above the formation of ester linkages between the C-14-hydroxylated anthracycline and pendant glycyl activated ester is avoided because of the absence of any organic base in the condensing process.

In another example, to prepare a polymer-bound anthracycline A in which Z is hydroxy, intermediate B as defined above in which $R_2$ is hydroxy in anhydrous dimethylsulfoxide, is treated with a peptidyl anthracycline 5 at room temperature for 15 hours. B is suitably employed at 14% w/v and 5 at 2.3% w/v. The conjugate is then precipitated with acetone, dissolved in absolute ethanol, typically at a concentration of 8% (w/w) and precipitated again with acetone to give a polymer-bound anthracycline of formula A as defined above.

The anthracycline content of the conjugates A is determined by analysis of the aglycone released from bound anthracycline by means of acid hydrolysis; thus, adriamycinone is the aglycone moiety of doxorubicin and 4'-epirubicin and 4-demethoxydaunomycinone is that of 4-demethoxydaunorubicin.

Polymer-bound-anthracyclines of the present invention exhibit good water solubility, biocompatibility, stability at physiological pH and release of the free active drug, $DNH_2$, after incubation with lysosomal enzymes.

Compounds of formula A exhibit enhanced antitumour activity in experimental models and reduced general toxicity when compared with free anthracycline.

The polymer-bound anthracyclines of formula A have anti-tumour activity. A human or animal can therefore be treated by a method comprising administering thereto a therapeutically effective amount of a polymer-bound anthracycline of formula A. The condition of the human or animal patient can thus be improved.

The dosage range adopted will depend on the route of administration and on the age, weight and condition of the patient being treated. The polymer-bound anthracyclines of formula A are typically administered by the parenteral route, for example intramuscularly, intravenously or by bolus infusion. A suitable dose range is from 5 to 800 mg/m² of anthracycline equivalent, for instance from 20 to 500 mg/m². A suitable regime entails administering a solution of 25 mg anthracycline equivalent /m2 intravenously at a volume of 10 ml/kg body weight over a 2 week period on days 5, 9 and 15.

The polymer-bound anthracyclines of formula A may be formulated into a pharmaceutical composition together with a pharmaceutically acceptable carrier or diluent. Typically the polymer-bound anthracyclines are formulated for parenteral administration, for example by dissolution in sterile water or water for injection.

The following Examples further illustrate the invention. Examples 1–6 relate to synthetic procedures for the preparation of monomers of formula 6 and 7 and polymeric intermediates of formula B.

EXAMPLE 1

[N-(methacryloylglycly)]2-hydroxypropylamide (6b)

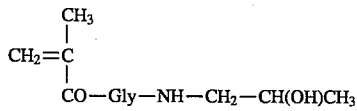

Methacryloylglycyl p-nitrophenyl ester (7a: 5.28 g, 20 mmol), prepared as described in Makromol. Chem. 178, 2159 (1977), was dissolved in anhydrous tetrahydrofurane (20 ml) and treated with 1-amino-2-hydroxypropane (3.2 ml, 40 mmol). After 20 minutes at room temperature, the solvent was removed under reduced pressure and the title compound 6b (3.3 g, yield 82.5%) was recovered after crystallization with acetone/ethyl ether. TLC on Kieselgel plate $F_{254}$ (Merck), eluting system methylene chloride/acetone (90:10 by volume) $R_f$=0.47.

EXAMPLE 2

[N-(methacryloylglycyl)]-hydroxyethylamide (6c)

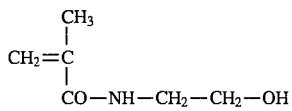

To a stirred mixture of 1-ethoxycarbonyl-2-ethoxy-1,2-dihydroquinoline (37 g, 0.15 mol) and aminoethanol (9.75 g, 0.15 mol) in anhydrous toluene (150 ml), methacrylic acid (14 ml, 0.165 mol) dissolved in anhydrous toluene (300 ml) was added dropwise in 15 minutes. The reaction mixture was stirred at room temperature for 24 hours. The title compound 6c was recovered after precipitation with n-hexane.

TLC on Kieselgel plate $F_{254}$ (Merck), eluting system methylene chloride/acetone (90:10 by volume) $R_f$=0.35.

EXAMPLE 3

[N-(methacryloylqlcyl)]2,3-dichloroophenyl ester (7b)

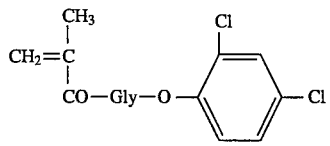

The title compound 7bwas prepared from methacryloylglycine (2.66 g, 20 mmol), prepared as described in Makromol. Chem. 178, 2159 (1977), and 2,4-dichlorophenol (3.26 g, 20 mmol) in anhydrous tetrahydrofurane (50 ml) and in presence of DCC (4.2 g, 21 mmol). Compound 7b (4.7 g, yield 82%) was crystallized from ethyl acetate and n-hexane.

TLC on Kieselgel 'plate $F_{254}$ (Merck), eluting system ethyl ether $R_f$=0.47.

EXAMPLE 4

Copolymer of N-methacryloylamide-2-hydroxypropane and N-methacryloylglycine (B2)

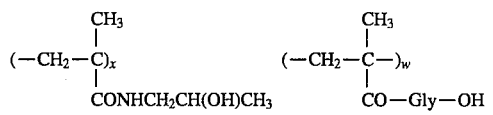

N-methacryloylamide-2-hydroxypropane (25.2 g, 0.18 mol), methacryloylglycine (2.86 g, 20 mmol) and α,α'-azoisobutirronitrile (5.9 g) were dissolved in anhydrous methanol (164 ml) The mixture was kept at 60° C. under nitrogen for 20 hours, then the reaction mixture was added to acetone (2000 ml) under stirring. The precipitate was collected, washed with acetone and dried to constant weight to give the title polymer B2 (26 g). Content of carboxy groups (w): 10 mol[{]jf44a
EXAMPLE 5

Copolymer of [N-(methacryloygylcyl)]2-hydroxypropanolamide and N-(methacryloylglycyl)2,4-dichlorophenyl ester (B3)

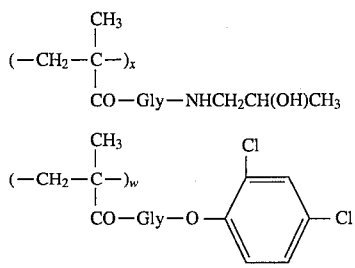

Compound 6b (14.4 g, 72 mmol) and compound 7b (5.19 g, 18 mmol) were polymerized in anhydrous acetone (300 ml) and in presence of α,α'-azoisobutirronitrile (1 g, 6 mmol) as described in Makromol. Chem. 178 2159 (1977) to the title compound B3. The polymeric material was recovered by filtration from the reaction mixture, dissolved in absolute ethanol and reprecipitated with acetone. Chlorine content: calculated 6.89 mol%, found 2.84 mol% (w)

EXAMPLE 6

Copolymer of [N-(methacryloylgylcyl)]-hydroxyethylamide and N-methacryloylglycine (B4)

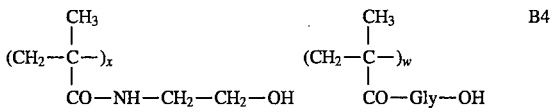

The title polymeric intermediate B4 was prepared from N-methacryloylamide-2-hydroxyethane (6c: 23.2 g, 0.18 mol), methacryloylglycine (2.86 g, 20 mmol) and α,α'-azoisobutirronitrile (5.9 g) in anhydrous methanol (164 ml) as described in Example 2. Content of carboxy groups (w): 10 %

Examples 7–12 relate to methods for the preparation of peptidyl-anthracyclines of formula 5

EXAMPLE 7

N-trityl-L-Phenylalanyl-L-Leucylglycyl 4-nitrophenylester

N-trityl-L-Phenylalanine (20.3 g, 50 mmol), prepared as described in J.Org. Chem. 47, 1324 (1982) was dissolved in anhydrous terahydrofurane (150 ml) and added with anhydrous N-hydroxybenzotriazole (8 gr). The mixture was cooled at 0° C. and treated with 1,3-dicyclohexylcarbodiimide (11.7 gr, 50 mmol) and, after 10 minutes, added dropwise with a solution of L-Leucylglycine ethylester p-toluensulphonate salt (20 g, 50 mmol) in in a mixture of anhydrous tetrahydrofurane (100 ml) and N-methylmorpholine (7 ml). The reaction mixture was kept at 0° C. for one hour and overnight at room temperature, then was filtered and the solvent was removed under reduced pressure. The crude material, dissolved with ethyl acetate, was washed in sequence with cooled 5% aqueous citric acid (3×100 ml), cooled 5% aqueous sodium bicarbonate and water, then concentrated and chromatographed on silica gel eluting with a mixture of methylene chloride and methanol (99:1 by volume) to give N-trityl-L-Phenylalanyl-L-leucylglycine ethyl ester (18 g, 30 mmol) that was converted into the corresponding acid 8a (17 g) by treatment in ethyl alchool 95% (400 ml) with 1N sodium hydroxide (30 ml) for two hours at room temperature.

TLC on Kieselgel plate F$_{254}$ (Merck), eluting system methylene chloride/methanol (80:20 by volume) R$_f$=0.53

$^1$H-NMR (200 MHz, CDCl$_3$) 0.88 (d, J=5.9 Hz, 6H, δ+δ'Leu); 1.2–1.6 (m, 3H, β+_Leu); 2.00 (dd,J=5.7 Hz, J=13.4 Hz, 1H, βPhe); 2.83 (dd, J=5.2 Hz, J=13.4 Hz, 1H, β'Phe); 3.51 (t, J=5.4, 1H, αPhe); 3.99 (d, J=4.4 Hz, 2H, α+α'Gly); 4.55 (m, 1H, αLeu); 6.8–7.4 (m, 22H, NHgly, NHLeu, 4—C$_6$H$_5$).

Compound 8a was dissolved in anhydrous tetrahydrofurane (450 ml) and added with p-nitrophenol (5.5 g, 40 mmol). The mixture was cooled at 0° C., added dropwise with a solution of 1,3-dicyclohexylcarbodiimide (8.24 g, 40 mmol) and kept overnight at 4° C. After that, the reaction mixture was filtered and the solvent removed under reduced pressure. The residue was dissolved with ethyl acetate and cooled at 0° C. After one hour the mixture was filtered and the solvent removed to afford, after crystallization from ethyl ether, the title compound 9a (20 g, yield 97%). TLC on Kieselgel plate F$_{254}$ (Merck), eluting system ethyl ether, R$_f$=0.80.

FD-MS: m/z 699 [M+H]$^{30}$ $^1$H-NMR (200 MHz, CDCl$_3$) 0.86 (d, J=6.2 Hz, 3H, δLeu); 0.88 (d, J=6.4 Hz, 3H, δ'Leu); 1.2–1.8 (m, 3H, β+_Leu); 1.90 (dd, J=5.9 Hz, J=13.5 Hz, 1H, βPhe); 2.89 (dd, J=4.6 Hz, J=13.5 Hz, 1H, β'Phe); 3.52 (dd, J=4.6 Hz, J=5.9 Hz, 1H, αPhe); 4.0–4.4 (m, 3H, αLeu, α+α'Gly); 6.78 (t, J=5.7 Hz, 1H, NHGly); 7.04 (d, J=7.7 Hz, 1H, NHLeu); 6.8–7.4 (m, 22Hz, 4—C$_6$H$_5$ and 2,6

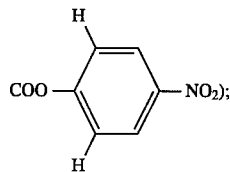

8.25 (m, 2H, 5,5

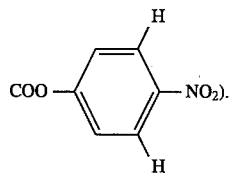

EXAMPLE 8

N-trityl-Glycyl-L-phenylalanyl-L-leucylglycyl p-nitrophenyl ester (C$_6$H$_5$)$_3$C-Gly-L-Phe-L-Leu-Gly-OC$_6$H$_4$pNO$_2$      (9b)

Intermediate N-trityl-L-Phenylalanyl-L-Leucylglycyl ethyl ester (6 g, 10 mmol), prepared as described in Example 7, was treated with aqueous 75% acetic acid at room temperature for one hour to give L-Phenylalanyl-L-leucylglycyl ethyl ester which was condensed with N-trityl-Glycine (3 g, 10 mmol) in presence of N-hydroxybenzotriazole and 1,3-dicyclohexylcarbodiimide to afford, after hydrolysis of ethyl ester and activation with p-nitrophenol as described in Example 7, the title compound 9b (3.8 g, yield 50%).

TLC on Kieselgel plate F$_{254}$ (Merck), eluting system ethyl ether, R$_f$=0.63. FD-MS: m/z 755 [M+H]$^+$

EXAMPLE 9

3'-N-(Gylcyl-L-leucyl-L-phenylalanyl) doxorubicin (5a)

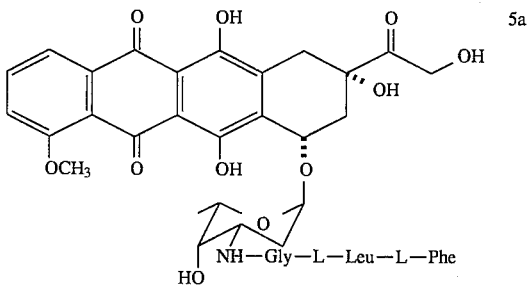

Doxorubicin hydrochloride (2.9 g, 5 mmol) dissolved in anhydrous dimethylformamide (50 ml) and triethylamine (0.5 ml), was reacted with N-trityl-Phenylalanylleucylglycyl p-nitrophenylester (9a: 3.5 g, 5 mmol) prepared as described in Example 7. The reaction mixture was kept overnight at room temperature, then precipitated with a mixture 1:1 of ethyl ether and n-hexane. The solid was purifyied through silica gel column eluting with a mixture of methylene chloride and methanol (98:2 by volume) to give N-protected peptidyl doxorubicin 10a (4.6 g), TLC on Kieselgel plate F$_{254}$ (Merck), eluting system methylene chloride/methanol (95:5 by volume) R$_f$=0.35.

FD-MS: m/z 1103 [M+H]$^+$

Compound 10a was dissolved with aqueous 75% acetic acid (250 ml) at room temperature for one hour, then diluted with a mixture 1:1 of water and methylene chloride (2500 ml) and brought to pH 7 with solid sodium bicarbonate. The organic phase was separated and the solvent removed under reduced pressure to give the title compound 5a (3.45 g, yield 80%). TLC on Kieselgel plate F$_{254}$ (Merck), eluting system methylene chloride/methanol/acetic acid/water (80:20:7:3 by volume) R$_f$=0.5. FD-MS: m/z 861 [M+H]$^+$ $^1$H-NMR (400 MHz, DMSO) 0.80 (d, J=6.4 Hz, 3H, δLeu); 0.83 (d, J=6.4 Hz, 3H, δ'Leu); 1.10 (d, J=6.8 Hz, 3H, 6'CH$_3$); 1.3–1.6 (m, 4H, β+_Leu and 2'eqH); 1.83 (ddd, J=2.8 Hz, J=13.2 Hz, J=13.2 Hz, 1H, 2'axH); 2.09 (dd, J=6.0 Hz, J=14.5 Hz, 1H, 8 axH); 2.18 (d, J=14.5 Hz, 1H, 8-eq); 2.8–3.2 (m, 4H, 10CH$_2$ and βPhe); 3.36 (m, 1H, 4'); 3.64 (m, 2H, αGly); 3.95 (s, 3H, OCH$_3$); 3.9–4.1 (m, 2H, 3'and αPhe); 4.15 (q, J=6.4 Hz, 1H, 5'H); 4.29 (q, J=7.7 Hz, 1H, αLeu); 4.55 (s, 2H, 14CH$_2$); 4.7–5.0 (m, 3H, 7H and 14 OH); 5.20 (d, J=3.4 Hz, 1H, 1'H); 5.46 (s, 1H, 9OH); 7.1–7.3 (m, 5H, Ar-Phe); 7.54 (d, J=8.5 Hz, 1H, 3'NH); 7.63 (m, 1H, 3H); 7.88 (m, 2H, 1H); and 2H); 8.17 (m, 4H, NH$_3$+ and NHGly); 8.70 (d, J=8.1 Hz, 1H, NHLeu); 13.23 (s, 1H, 11 OH); 14.00 (s, 1H, 6OH).

EXAMPLE 10

3'-N-((Glycyl-L-leucyl-L-phenylalanylglycyl)doxorubicin (5b)

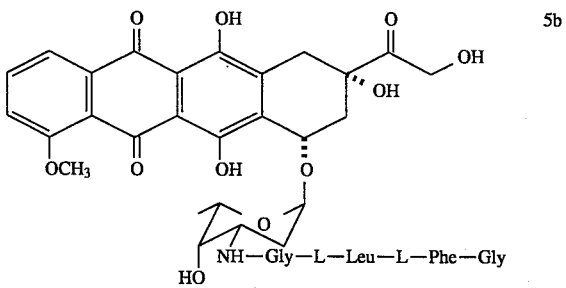

Doxorubicin hydrochloride (2.9 g, 5 mmol) was reacted with N-trityl-Glycyl-L-phenylalany-L-leucyllglycyl p-nitrophenyl ester (9b: 3.8 g, 5 mmol), prepared as described in Example 8, and then treated with aqueous 75% acetic acid as described in Example 9, to give the title compound 5b (4 g, yield 90%).

TLC on Kieselgel plate $F_{254}$ (Merck), eluting system methylene chloride/methanol/acetic acid/water (80:20:7:3 by volume) $R_f$=0.44. FD-MS: m/z 938 $[M+H]^{30}$

EXAMPLE 11

4-demethoxy-3'-N-(Glycyl-L-leucyl-L-phenylalanyl) daunorubicin (5c)

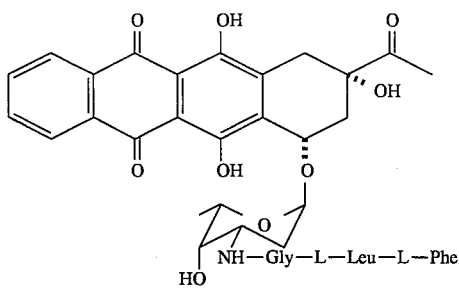

The title compound 5c (3 g, yield 75%) was prepared from 4-demethoxydaunorubicin hydrochloride (2.9 g, 5 mmol) and N-trityl-Phenylalanylleucylglycyl p-nitrophenylester (9a: 3.5 g, 5 mmol) following the same procedure described in Example 9. TLC on Kieselgel plate $F_{254}$ (Merck), eluting system methylene chloride/methanol/acetic acid/water (80:20:7:3 by volume) $R_f$=0.51.

FD-MS: m/z 815 $[M+H]^+$ $^1$H-NMR (200 MHz, CDCl$_3$) 0.84 (d, J=6.0 Hz, 3H, δLeu); 0.88 (d, J=6.0 Hz, 3H, δ'Leu); 1.27 (d, J=6.4 Hz, 3H, 6'CH$_3$); 1.4–1.7 (m, 3H, β+Leu); 1.7–2.0 (m, 2H, 2'CH$_2$); 2.06 (dd, J=4.2H, J=14.9 Hz, 1H, 8axH); 2.32 (d, J=14.9 Hz, 1H, 8eqH); 2.40 (s, 3H, COCH$_3$); 2.70 (dd, J=8.6 Hz, J=13 Hz, 1H, βPhe); 3.12 (dd, J=4.2 Hz, J=13.7 Hz, 1H, β'Phe); 2.94, 3.23 (two d, J=19.2 Hz, 2H, 10CH$_2$); 3.5–3.8 (m, 3H, 4'H, αPhe and αGly); 3.9–4.3 (m, 4H, α'Gly, αLeu, 5'H, 3' H); 5.19 (m, 1H, 7H); 5.45 (d, J=2.7 Hz, 1H, 1'H); 6.9–8.4 (m, 12H, 1H, 2H, 3H, 4H, ArPhe, 3'NH, NHGly, NHLeu).

EXAMPLE 12

4'-epi-3'-N-(Glycyl-L-Leucyl-L-phenylalanyl)doxorubicin (5d)

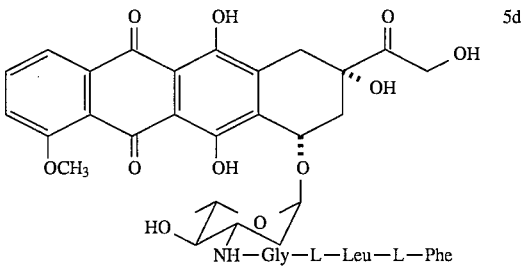

The title compound 5d (3.25 g, yield 86%) was prepared from 4'-epidoxorubicin hydrochloride (2.9 g, 5 mmol) and N-trityl-Phenylalanylleucylglycyl P-nitrophenyl ester (9a: 3.5 g, 5 mmol) following the same procedure described in Example 9. TLC on Kieselgel plate $F_{254}$ (Merck), eluting system methylene chloride/methanol/acetic acid/water (80:20:7:3 by volume) $R_f$=0.46. FD-MS: m/z 861 $[M+H]^+$ $^1$H-NMR (400 MHz, DMSO) 0.79 (d, J=6.3 Hz, 3H, δLeu); 0.81 (d, J=6.3 Hz, 3H, δ'Leu); 1.19 (d, J=5.9 Hz, 3H, 6'CH$_3$); 1.3–1.6 (m, 4H, 2'Hax, β,β'Leu, _Leu); 1.82 (dd, J=4.7 Hz, J=12.5 Hz, 1H, 2'Heq); 2.1–2.3 (m, 2H, 8—CH$_2$); 2.59 (dd, J=8.2 Hz, J=13.7 Hz, 1H, βPhe); 2.9–3.1 (m, 4H, β'Phe, 10—CH$_2$, h'H); 3.41 (dd, 4.7 Hz, J=8.2 Hz, αPhe); 3.54 (dd, J=5.5 Hz, J=16.4 Hz, 1H, αGly); 3.67 (dd, J=6.2 Hz, J=16.4 Hz, 1H, α'Gly); 3.80 (m, 1H, 3'H); 3.90 (m, 1H, 5'H); 3.95 (s, 3H, OCH$_3$) 4.18 (m, 1H, αLeu); 4.55 (m, 2H, 14—CH$_2$); 4.3–5.0 (m, 3H, 14—OH, 7H, 4'—OH 5.17 (d, J=3.1 Hz, 1H, 1'H); 5.46 (s, 1H, 9—OH); 7.1–7.3 (m, 5H, Ar-Phe); 7.53 (d, J=8.2 Hz, 1H, NH—Gly); 7.60 (m, 1H, 3H); 7.86 (m, 2H, 1H, 2H); 8.05 (d, J=6.4 Hz, 1H, NH—Leu); 8.11 (t, J=5.9 Hz, 1H, NH—Gly).

EXAMPLE 14

Copolymer of 3-methacryloylamino-2-hydroxyprodane, 3'-N-(methacryloyqlycyl-L-phenylalanyl-leucylglycyl-)doxorubicin and (N-methacryloylglycyl) 2-hydroxypropanolamide (A2)

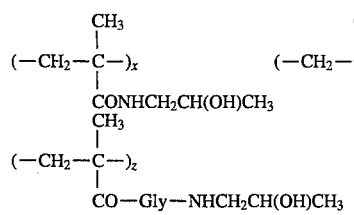

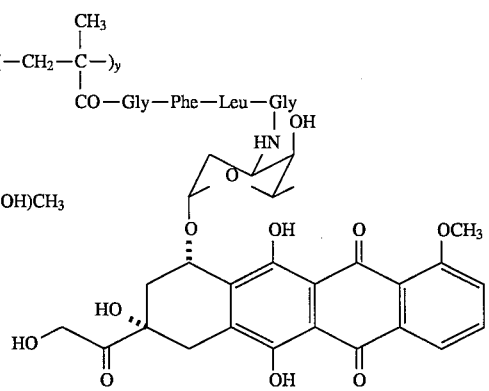

Polymeric precursor B1 (10 g, 2.7×10⁻³ eq of p-nitrophenyl ester), prepared as described in Makromal. Chem. 178, 2159 (1977), was dissolved in dry dimethylformamide (60 ml) and added with 3'-N-(Glycyl-leucyl-L-phenylalanyl)doxorubicin (5a: 1.53 g 1.72 mmol). The mixture was kept under stirring at room temperature for 24 hours, then added with 1-aminopropanol (0.13 ml). After one hour, the reaction mixture was added to a stirred mixture of acetone/ethyl ether (1.2 1, 3/1 by volume) and flitrated. The precipitate was disolved with ethanol (150 ml) and precipitated with acetone/ethyl ether (1.2 1, 4/1 by volume) to give polymeric compound of formula A2 (10 g).

Doxorubicin.HCl content: 9% (w/w).

Examples 13–18 illustrate the procedures for the preparation of Polymer-bound-anthracyclines of formula A.

EXAMPLE 13

Copolymer of 3-methacryloylamino-2hydroxypropane, 3'-N-(methacryloylgly-L-phenlalanyl-L-leucylqlycyl)doxorubicin and N-methacryloylqlycine (A1)

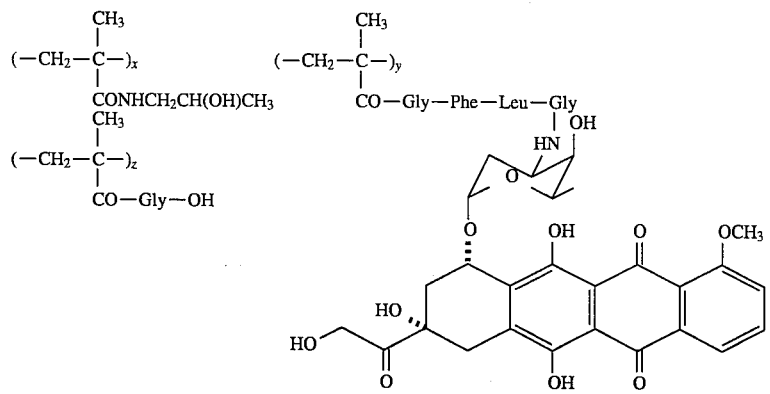

Polymeric precursor B2 (7,15 g, 5 mmol of —COOH), prepared as described in Example 4, and 3'-N-(Glycyl-leucyl-L-phenylalanyl)doxorubicin (5a: 2,36 g, 2,5 mmol) were dissolved in anhydrous dimethylformamide (100 ml), then added with N-ethoxycarbonyl-2-ethoxy-1,2-dihydroquinoline (0.7 g, 2,5 mmol). The mixture was kept under stirring at room temperature for 24 hours, then poured in ethyl ether (800 ml). The precipitate was dissolved with ethanol (100 ml), precipitated with acetone (800 ml) and dried to constant weight to give the title compound A1 (7 g).

Doxorubicin.HCl content: 9% (w/w).

EXAMPLE 15

Copolymer of 3-methacryloylamino-2-hyvdroxypropane, 4-demethoxy, 3'-N-(methacrylgylcyl-L-phenylalanyl-L-leucyl glycyl)daunorubicin and N-methacryloylglycine (A3)

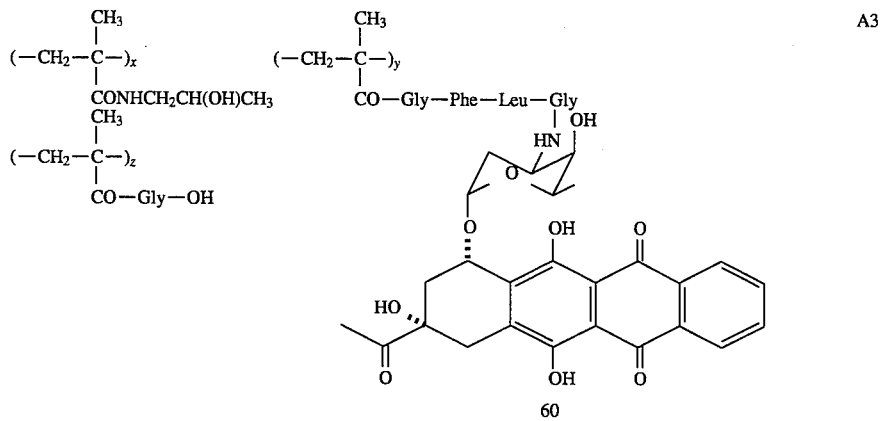

4-demethoxy-3'-N-(Glycyl-L-leucyl-L-phenylalanyl)daunorubicin (5d: 1.48 g, 1.72 mmol) was reacted with polymeric precursor B2 (10 g) in presence of N-ethoxycarbonyl-2-ethoxy-1,2-dihydroquinoline (0.48 g) in anhydrous dimethylformamide, as described in Example 13, to afford the title compound A3.

4-demethoxydaunorubicin.HCl content: 9% (w/w).

EXAMPLE 16

Copolymer of 3-methacryloylamino-2-hydroxypropane, 4'-epi-3'-N-(methacryloylglycyl-L-phenylalanyl-L-leuculglycyl)doxorubicin and 1-N-(methacryloylgylcyl)-2-hydrocypropane (A4)

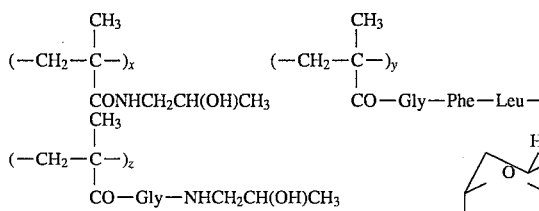
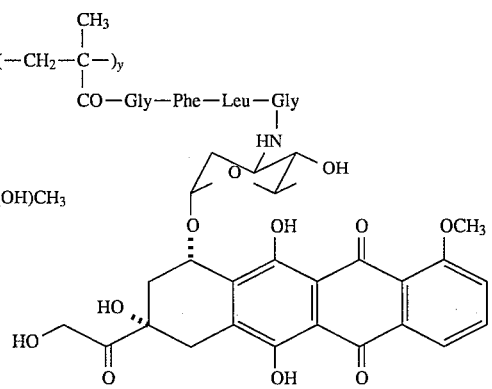

A4

4'-epi-3'-N-(Glycyl-L-leucyl-L-phenylalanyl)doxorubicin (5e: 1.48 g, 1.72 mmol) was reacted with polymeric precursor B1 followed by 1-aminopropanol (0.13 ml) as described in Example 14 to give 4'-epi-doxorubicin polymer conjugate of formula A4 (10 g).

4'-epidoxorubicin.HCl content: 9% (w/w).

EXAMPLE 17

Copolymer of 3-methacryloylamino-2-hydroxypropane, 4'-epi-3'-N-(methacryloylqlycyl-L-phenylalanyl-L-leucylglycvl)doxorubicin N-methacryloylglycine (A5)

carbonyl-2-ethoxy-1,2-dihydroquinoline, in anhydrous dimethylformamide.

EXAMPLE 18

Copolymer of [N-(methacryloylgylcyl)]-hvdroxyethylamide, 3'-N-(methacryloylglycyl-L-phenylalanyl-L-leucylglycyl)doxorubicinand N-methacryloylglycine (A6)

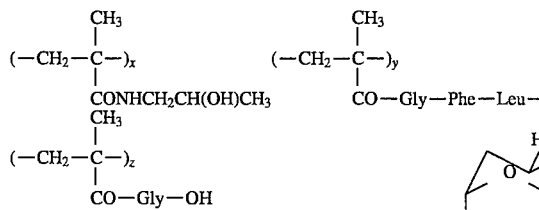
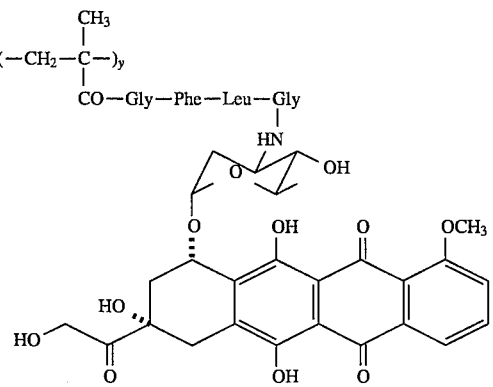

A5

The title compound was prepared as described in Example 13, from polymeric intermediate B2, 4'-epi-3'-N-(Glycylleucyl-L-phenylalanyl) doxorubicin (5e) and N-ethoxy-

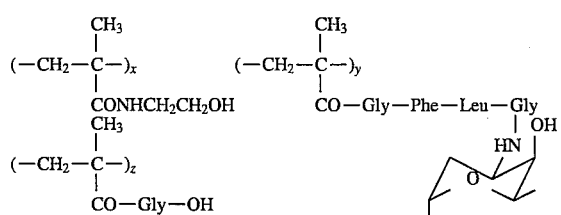
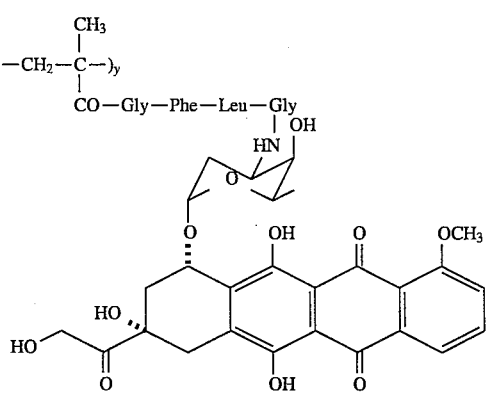

A6

The title doxorubicin polymeric prodrug A6 was prepared by condensing polymeric intermediate B4 and 3'-N-(Glycyl-leucyl-L-phenylalanyl)doxorubicin (5e) and N-ethoxycarbonyl-ethoxy-1,2-dihydroquinoline, in anhydrous dimethylformamide as described in Example 13.

EXAMPLE 19

Antitumour activity of compound A1 on M5076.

The antitumour activity of A1, described in Example 13, was tested as follows:

Materials and Methods

1. Drug Administration.

All drug solutions were prepared immediately before use. Treatment was administered i.v. in a volume of 10 ml/Kg body weight at days 5,9 and 15.

Anthracyclines were dissolved in sterile water and the concentration was checked spectrophotometrically.

Lyophylized polymers were dissolved in water to give a starting solution of 25 mg anthracycline equivalent/ml according to the reported concentration, further dilutions were performed in water.

2. Solid Tumor.

M5076 murine reticulosarcoma was obtained by serial i.m. passage and transplanted ($5 \times 10^5$ cells/mouse) s.c. in C75 B1/6 mice to evaluate the activity on primary tumor.

3. Evaluation of Antitumor Activity and Toxicity.

Tumor growth was assessed by caliper measurement, and the tumor weight estimated according to Geran etal., see Cancer Chemother. Rep. 3, 1 (1972).

The antitumor activity was determined in time (days) to reach one gramm tumor weight and is reported as tumor growth delay (TGD).

The median increase in survival time (T/C%) was calculated using the following formula:

$$T/C\% = \frac{\text{median survival time treated group}}{\text{median survival time controls}} \times 100$$

Toxicity was evaluated on the basis of body weight reduction and gross finding main of spleen and liver reduction.

Neurotoxicity is determined as number of mice with lack of motor function.

The results are set out in Table 1:

TABLE 1

| compound | Dose[1] mg/kg | TDG[2] (1 g) | A.U.C. % inhib | T.C.[3] % | Tox[4] | LTS[5] | Tumor[6] free |
|---|---|---|---|---|---|---|---|
| control | — | 15 | | | | 0/10 | 0/10 |
| doxo- | 7.5 | 35 | 90 | 148 | 0/26 | 0/26 | 0/26 |
| rubicin | 10.0 | 39 | 100 | 153 | 3/26 | 0/26 | 0/26 |
| A1 | 30.0 | 80 | 100 | 378 | 0/10 | 4/10 | 3/10 |
| | 40.0 | nd | 100 | >369 | 0/10 | 6/10 | 5/10 |
| | 50.0 | nd | 100 | >369 | 2/10* | 7/10 | 7/10 |

$5 \times 10^5$ cells/mouse were injected sc
nd = not determined
*Neurotoxicity
[1]Treatment was given on day 5, 9, 15
[2]TDG = Tumor Growth Delay
[3]Median survival time of treated mice/median survival time of control group × 100
[4]Number of toxic deaths/total number of mice
[5]Long Terms Survivors
[6]Mice with tumor free at the end of the experiments

EXAMPLE 20

Antitumour activity of compound A3 of M5076.

The antitumour activity of A3, described in Example 15, was tested using the method and materials of Example 19. The results are shown in Table 2:

TABLE 2

| compound | Dose[1] mg/kg | TDG[2] (1 g) | A.U.C. % inhib | T.C.[3] % | Tox[4] | LTS[5] | Tumor[6] free |
|---|---|---|---|---|---|---|---|
| control | — | 15 | | | | 0/10 | 0/10 |
| 4-de- | 1.0 | 19 | 47 | 142 | 0/9 | 0/9 | 0/9 |
| methoxy- | 1.5 | 28 | 80 | 160 | 0/9 | 0/9 | 0/9 |
| dauno- | | | | | | | |
| rubicin | | | | | | | |
| A3 | 4.0 | 49 | 100 | 198 | 0/10 | 0/10 | 0/10 |
| | 5.0 | 50 | 100 | 205 | 0/10 | 0/10 | 0/10 |
| | 6.0 | 55 | 100 | 212 | 0/9 | 0/9 | 0/9 |

$5 \times 10^5$ cells/mouse were injected sc
*Neurotoxicity
[1]Treatment was given on day 5, 9, 15
[2]TDG = Tumor Growth Delay
[3]Median survival time of treated mice/median survival time of control group × 100

TABLE 2-continued

| compound | Dose[1] mg/kg | TDG[2] (1 g) | A.U.C. % inhib | T.C.[3] % | Tox[4] | LTS[5] | Tumor[6] free |
|---|---|---|---|---|---|---|---|

[4]Number of toxic deaths/total number of mice
[5]Long Terms Survivors
[6]Mice with tumor free at the end of the experiments Antitumor activity of compound A4 (copolymer of 3-methacryloyamino-2-hydroxypropane,4'-epi-3'-N(methacrylglycyl-L-phenylalanyl-L-leucylglycyl)doxorubicin and 1-N-(methacryloylglycyl)-2-hydroxypropane) in comparison with 4'-epidoxorrubicin.HCl.

The antitumor activity was tested with the same treatment schedule for 4'-epidoxorubicin.HCl and compound A4.

Against early M5076 murine reticulosarcoma, compound A4 was more active than free drug at all tested doses (Table 3).

TABLE 3

Antitumor activity of compound A4 in comparison with 4'-epidoxorubicin.HCl against M5076 murine rituculosarcoma.

| compound | Dose[1] mg/kg | TDG[2] (1 g) | A.U.C. % inhib. | T.C.[3] % | TOX[4] |
|---|---|---|---|---|---|
| 4'-Epidoxo-rubicin.HCl | 5 | 22 | 51 | 105 | 0/9 |
|  | 7.5 | 34 | 90 | 124 | 0/9 |
|  | 10 | 40 | 99 | 125 | 0/9 |
| A4 | 10 | 62 | 100 | 190 | 0/9 |
|  | 20 | 62 | 100 | 219 | 0/9 |
|  | 30 | 71 | 100 | 229 | 0/9 |

$5 \times 10^5$ cells/mouse were injected sc.
[1]Treatment was given on day 5, 9, 15
[2]TDG = Tumor Growth Delay
[3]Median survival time of treatment mice/median survival time of control group × 100
[4]Number of toxic deaths/total number of mice Toxicity of compound A4 (copolymer of 3-methacryloylamino-2-hydroxypropane, 4'-epi-3'-N(methacryloylglycyl-L-phenyl-alanyl-L-leucylglycyl)doxorubicin and 1-N-(methacryloylglycyl)-2-hydroxypropane) in comparison with 4'-epidoxorubicin.HCl.

Toxicity was evaluated in healthy C57B1F mice, treatment i.v., with single doses of 4'-epidoxorubicin.HCl (13.2–16.15–19–20.6–25.2 and 33.2 mg/kg) and compound A4 (50–63–79–100–120–140 mg/kg)

For the determination of $LD_{10}$ and $LD_{50}$ in healthy C57 B1F mice the Probit Analysis' after 3-week recovery was used.

The therapeutic index was calculated using the following formula:

$$\text{Therapeutic Index:} \frac{DE_{50}}{LD_{50}} \quad \frac{\text{(Dose effective 50)}}{\text{(Lethal Dose 50)}}$$

Dose effective 50 is the dose causing 50% of tumor growth reduction. Animal safety was observed for 90 days.

The $LD_{10}$ and $LD_{50}$ values in C57 B1/F mice are as follows:

| Compound | $LD_{10}$ (mg/kg) | $LD_{50}$ (mg/kg) |
|---|---|---|
| 4'-epidoxorubicin.HCl | 16.4 | 21.4 |
| A4 | 128.0 | 389 (extrapolated value) |

The low toxicity of compound A4 allows to administer higher doses of product and to reach equivalent or better results than with 4'-epidoxorubicin.HCl and to obtain a better therapeutic index. The terapeutic index for 4'-epidoxorubicin.HCl and compound A4 are respectively 3 and 40.

We claim:

1. A polymer-bound anthracycline, prepared by radically copolymerizing methacryloyl compounds of the following formulae 6 and 7:

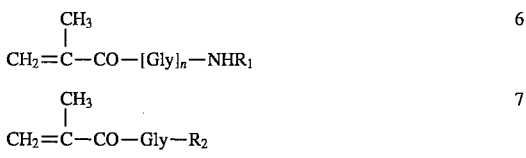

to form a copolymer, wherein the methacryloyl compounds of the formulae 6 and 7 are present in a molar ratio of from 98:2 to 70:30, respectively, then reacting the copolymer with an anthracycline aminoglycoside intermediate of formula 10:

to form said polymer-bound anthracycline, wherein:
Gly represents glycine;
n is 0 or 1;
$R^1$ is a $C_1$–$C_6$ alkyl group substituted by one or more hydroxy groups;
$R_2$ is a hydroxy group or a leaving group;
Y is an amino acid residue or a peptide spacer; and
NH—D is the residue of an anthracyline aminoglycoside $NH_2$—D.

2. The polymer-bound anthracycline of claim 1, having units represented by formulae 1, 2 and 3:

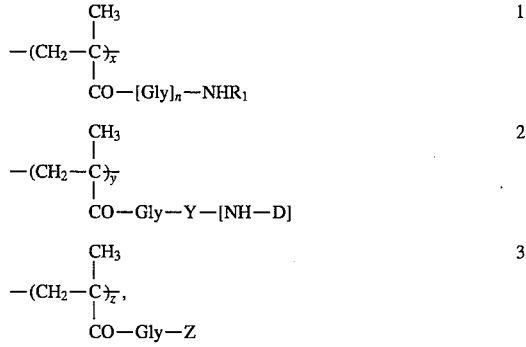

wherein:
x is from 70 to 98 mol %,
y is from 1 to 29 mol %,
z is from 1 to 29 mol %, and
Z is a hydroxy group or a residue of formula —$NHR_1$ wherein $R_1$ is a $C_1$–$C_6$ alkyl group substituted by one or more hydroxy groups.

3. The polymer-bound anthracycline of claim 1, wherein said anthracycline aminoglycoside has the following formula Q:

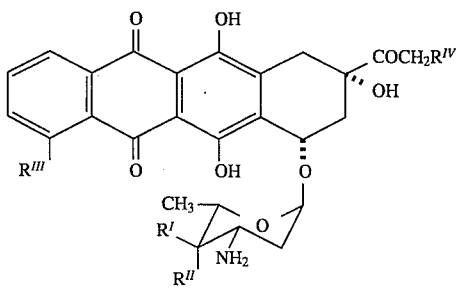

wherein one of R' and R'' is hydrogen and the other is a hydroxy group or iodine, R''' is hydrogen or OCH₃ and R'ᵛ is hydrogen or a hydroxy group.

4. The polymer-bound anthracycline of claim 2, in which x is from 90 to 98 mol %, y is from 1 to 10 mol % and z is from 1 to 10 mol %.

5. The polymer-bound anthracycline of claim 1, in which $R_1$ is a hydroxyethyl, 2-hydroxypropyl or 3-hydroxypropyl group.

6. The polymer-bound anthracycline of claim 1, in which Y is Gly-Phe-Gly, Gly-Leu-Gly, Phe-Leu-Gly, Gly-Phe-Leu-Gly or Leu-Leu-Gly.

7. The polymer-bound anthracycline of claim 1, in which $NH_2$—D is doxorubicin, 4'epidoxorubicin, 4-demethoxy-daunorubicin, idarubicin or 4'-iodo-4'-desoxydoxorubicin.

8. A process for preparing a polymer-bound anthracycline, comprising:
   (i) reacting a polymeric intermediate prepared by radically copolymerizing methacryloyl compounds of the following formulae 6 and 7:

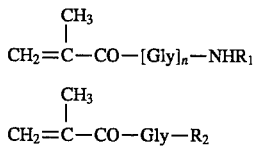

to form a copolymer, wherein the methacryloyl compounds of the formulae 6 and 7 are present in a molar ratio of from 98:2 to 70:30, respectively, then reacting the copolymer with an anthracyline aminoglycoside intermediate of formula 10:

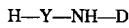

to form said polymer-bound anthracycline, wherein:
Gly represents glycine;
n is 0 or 1;
$R^1$ is a $C_1$–$C_6$ alkyl group substituted by one or more hydroxy groups;
$R_2$ is a hydroxy group or a leaving group;
Y is an amino acid residue or a peptide spacer; and
NH—D is the residue of an anthracyline aminoglycoside $NH_2$—D, and optionally,
   (ii) when $R_2$ is a leaving group, reacting the product of step (i) with a compound of formula $NH_2R_1$.

9. The process of claim 8, wherein said polymer-bound anthracycline has units represented by formulae 1, 2 and 3:

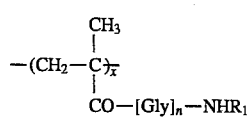

wherein:
x is from 70 to 98 mol %,
y is from 1 to 29 mol %,
z is from 1 to 29 mol %, and
Z is a hydroxy group or a residue of formula —$NHR_1$ wherein $R_1$ is a $C_1$–$C_6$ alkyl group substituted by one or more hydroxy groups.

10. An anthracycline derivative of the formula 5

$$HY—NH—D \qquad 5$$

wherein:
Y is Gly-Phe-Gly, Gly-Leu-Gly, Phe-Leu-Gly, Gly-Phe-Leu-Gly or Leu-Leu-Gly; and
NH—D is the rsidue of an anthracyline amingoglycoside $NH_2$—D.

11. The anthracycline derivative of claim 10, wherein said anthracycline amingoglycoside has the following formula Q:

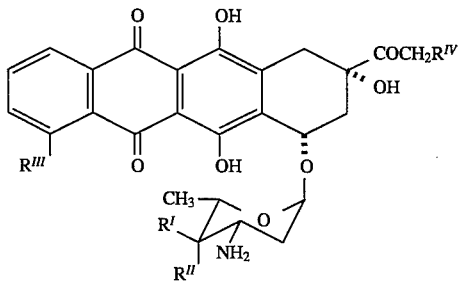

wherein one of R' and R'' is hydrogen and the other is a hydroxy group or iodine, R''' is hydrogen or OCH₃ and R'ᵛ is hydrogen or a hydroxy group.

12. The anthracycline derivative of claim 11, in which $NH_2$—D is doxorubicin, 4'epidoxorubicin, 4-demethoxy-daunorubicin, idarubicin or 4'-iodo-4'-desoxydoxorubicin.

13. A pharmaceutical composition comprising a pharmaceutically acceptable diluent or carrier and, as active ingredient, the polymer-bound anthracycline of claim 1.

14. A pharmaceutical composition comprising a pharmaceutically acceptable diluent or carrier and, as active ingredient, the anthracycline derivative of claim 10.

15. the process of claim 8, wherein $R_2$ is a p-nitrophenoxy or 2,4-dichlorophenoxy group.

* * * * *